US011419619B2

(12) United States Patent
Brouillette et al.

(10) Patent No.: US 11,419,619 B2
(45) Date of Patent: Aug. 23, 2022

(54) METHOD AND SYSTEM FOR TREATING LESIONS (71) Applicant: Les Solutions Medicales Soundbite Inc., Saint-Laurent (CA)

(72) Inventors: Martin Brouillette, Sherbrooke (CA); Steven Dion, Sherbrooke (CA); Louis-Philippe Riel, Montreal (CA)

(73) Assignee: Les Solutions Médicales Soundbite Inc., Saint-Laurent (CA)

( * ) Notice: Subject to any disclaimer, the term of this patent is extended or adjusted under 35 U.S.C. 154(b) by 103 days.

(21) Appl. No.: 16/312,799

(22) PCT Filed: Jun. 29, 2017

(86) PCT No.: PCT/IB2017/053942
§ 371 (c)(1),
(2) Date: Dec. 21, 2018

(87) PCT Pub. No.: WO2018/002887
PCT Pub. Date: Jan. 4, 2018

(65) Prior Publication Data
US 2019/0343539 A1 Nov. 14, 2019

Related U.S. Application Data

(60) Provisional application No. 62/357,024, filed on Jun. 30, 2016.

(51) Int. Cl.
*A61B 17/22* (2006.01)
*A61B 90/00* (2016.01)
(52) U.S. Cl.
CPC .................. *A61B 17/22012* (2013.01); *A61B 2017/22015* (2013.01); *A61B 2017/22024* (2013.01);
(Continued)

(58) Field of Classification Search
CPC ........ A61B 17/22012; A61B 2090/374; A61B 2090/376; A61B 2090/378;
(Continued)

(56) References Cited

U.S. PATENT DOCUMENTS 3,584,327 A * 6/1971 Murry .................... G10K 11/24
15/104.16
3,825,887 A * 7/1974 Murry ................ G01N 29/2462
367/138
(Continued)

FOREIGN PATENT DOCUMENTS

DE      3703336 A1    8/1988
EP      0351240 A2    1/1990
WO   2016170520 A1   10/2016

OTHER PUBLICATIONS

International Search Report; Canadian Intellectual Property Office; International Application No. PCT/IB2017/053942; dated Oct. 12, 2017; 6 pages.
(Continued)

*Primary Examiner* — Julian W Woo
(74) *Attorney, Agent, or Firm* — Taft Stettinius & Hollister LLP (57) ABSTRACT

A method of and a system for treating a lesion. A waveguide is inserted into a vessel of a subject, with the lesion being present in the vessel and the waveguide extending longitudinally between a proximal end and a distal end. The distal end of the waveguide is positioned adjacent to the lesion, and a high amplitude broadband mechanical pulse is generated and propagated from the proximal end to the distal end of the waveguide. At least a portion of the high amplitude broadband mechanical pulse is propagated from the distal end of the waveguide to the lesion, with the at least
(Continued)

a portion of the high amplitude broadband mechanical pulse propagating up to the lesion, thereby treating at least partially the lesion.

33 Claims, 3 Drawing Sheets

(52) U.S. Cl.
CPC ... *A61B 2090/374* (2016.02); *A61B 2090/376* (2016.02); *A61B 2090/378* (2016.02); *A61B 2090/3983* (2016.02)

(58) Field of Classification Search
CPC .. A61B 2090/3983; A61B 2017/22015; A61B 2017/22024; A61B 2017/22014
See application file for complete search history.

(56) References Cited

U.S. PATENT DOCUMENTS

| | | | | |
|---|---|---|---|---|
| 3,937,990 | A * | 2/1976 | Winston | A61C 3/03 310/325 |
| 4,972,826 | A * | 11/1990 | Koehler | G10K 11/02 367/152 |
| 4,989,588 | A * | 2/1991 | Kubota | A61B 17/22012 601/4 |
| 5,344,395 | A * | 9/1994 | Whalen | A61B 17/320783 606/159 |
| 6,007,499 | A * | 12/1999 | Martin | A61B 8/4254 601/3 |
| 6,488,639 | B1 * | 12/2002 | Ribault | A61N 7/02 600/439 |
| 6,599,256 | B1 * | 7/2003 | Acker | A61D 1/06 600/439 |
| 7,520,856 | B2 * | 4/2009 | Vaezy | A61B 8/08 600/439 |
| 8,444,579 | B2 * | 5/2013 | Sliwa | A61N 7/02 601/2 |
| 8,696,612 | B2 * | 4/2014 | Wilson | A61M 37/0092 604/22 |
| 9,119,952 | B2 * | 9/2015 | Gertner | A61B 8/06 |
| 10,350,004 | B2 * | 7/2019 | Gifford, III | A61B 18/1492 |
| 10,656,025 | B2 * | 5/2020 | Kanz | G01K 7/02 |
| 11,000,880 | B2 * | 5/2021 | Riel | A61B 17/22012 |
| 2005/0043753 | A1 * | 2/2005 | Rabiner | A61B 17/22012 606/159 |
| 2013/0096545 | A1 | 4/2013 | Laudenslager et al. | |
| 2013/0158453 | A1 | 6/2013 | Brouillette et al. | |
| 2014/0031800 | A1 | 1/2014 | Ben Oren et al. | |
| 2014/0277002 | A1 | 9/2014 | Grace | |

OTHER PUBLICATIONS

Written Opinion of the International Searching Authority; Canadian Intellectual Property Office; International Application No. PCT/IB2017/053942; dated Oct. 12, 2017; 6 pages.

* cited by examiner

METHOD AND SYSTEM FOR TREATING LESIONS

CROSS REFERENCE TO RELATED APPLICATIONS

This application is a U.S. National Phase of International PCT Application No. PCT/IB2017/053942 filed Jun. 29, 2017, which claims the benefit of U.S. Provisional Application No. 62/357,024 filed Jun. 30, 2016, the contents of each application hereby incorporated by reference in their entirety.

TECHNICAL FIELD

The present invention relates to the field of methods and systems for treating blood vessel lesions, and more particularly to methods and systems for treating lesions using mechanical waves.

BACKGROUND

Cardiovascular disease remains a leading cause of death worldwide. Atherosclerosis consists of plaque accumulation along the inner wall of arteries. This can reduce the size of the flow passage and this is known as stenosis. When the blood vessel is completely blocked this is known as an occlusion. The reduction in blood flow due to lesions such as stenosis or occlusion can impair or harm the tissues and organs relying on this blood flow. The blood flow through these lesions can be restored through procedures known as percutaneous transluminal angioplasty (PTA) techniques. In many cases the lesion contains hard calcified structures and dense fibrotic tissues that may be difficult to treat using traditional PTA techniques and apparatuses, and together with the vessel size and tortuosity, may be the cause of the potential complications. Some experts therefore believe that new devices and technologies in the field of PTA may improve the success rate and reduce the procedure time for restoring blood flow through calcified and/or fibrotic lesions.

Over the years, various apparatus and methods have been developed and proposed to help in blood vessel recanalization of calcified and/or fibrotic lesions through minimally invasive procedures. For example, devices have used a mechanical impactor with or without the use of a transmission member, a narrowband ultrasonic source with a transmission wire, and various other methods of energy deposition near the lesion.

For procedures performed using a mechanical impactor, a projectile is accelerated and impacts a proximal end of a transmission member or a distal cap that is in direct contact with the lesion. The projectile can be accelerated using a pneumatic source, a solenoid, a mechanical spring or other means. The mass of the projectile and its speed at impact produce high stresses at the impact surface and therefore require commensurate maintenance. Also, this method may offer very limited control over the parameters of the mechanical pulse that is generated. Moreover, such devices may be noisy and may lack durability.

Another prior art example consists in a system comprising an ultrasonic wire excited at resonance with a horn and an electromechanical transducer. This constitutes a first example associated with the use of a narrowband source. This arrangement is used to amplify the displacement at the distal end of the device in contact with the lesion. The ultrasonic wire is usually used inside a dedicated catheter with cooling fluid circulation to prevent overheating of the device. By doing so, the device becomes bulkier and thus is limited in its ability to reach lesions in small and tortuous anatomy. Considerable loss (due to signal distortion and nonlinearity) and/or mode conversion (from axial to transverse) may also occur at a bend when the device is activated. The frequency of operation (typically around 20 kHz) may create large stress, strain and heat at the ultrasonic wire junction with the horn and within the ultrasonic wire itself. This may contribute to weaken the ultrasonic wire resulting in higher risk of failure.

Other prior art forms of energy deposition can be used near the lesion. For example, electromechanical transducer(s) can be used at or near the distal end of a catheter to produce mechanical waves near the lesion. Such a method may be limited in terms of the power that can be generated considering its miniature size. Moreover, the fabrication of this transducer may be complex and expensive especially considering that the device must be discarded after utilization to prevent contamination. Also, electrical wires are needed to drive the transducer(s) which can leak current inside the body and impact normal heart rhythm.

Laser energy may be used with optical fibers to effectively deliver pulses of high intensity light at the lesion. However, the inherent fragility of optical fibers makes them prone to break, especially when used in tortuous anatomy. Moreover, this form of energy, i.e., heat deposition, may be difficult to control and thus be unsafe to nearby healthy tissues; this also necessitates costly laser sources.

Radiofrequency (RF) energy is another prior art source of energy that can be delivered at the lesion site using electrodes and high voltage (i.e. 1 kV or higher). Like laser energy, RF energy may be limited in terms of control capability and may tend to create large heat deposition resulting in damage to nearby healthy tissues. Electrical spark discharge can also be used to generate shockwaves near the lesion, which requires even higher voltages (i.e., greater than 2 kV). For certain designs, erosion and mechanical wear of the electrodes may represent safety and reliability issues. Furthermore, for safety issues, devices using electrical discharges in the heart need to be synchronized with the subject's heart rhythm, which must thus be predictable and constant.

Chemical detonations can also be used to accelerate a distal hard mass causing it to impact a nearby lesion. Chemical reactions may be difficult to control and contain, especially in in-vivo environments. Toxic and potentially hazardous products can also be associated with detonations and explosions.

Therefore, it appears that impactors, narrowband energy sources and other prior art methods of energy deposition near vascular lesions all present drawbacks.

Therefore, there is a need for an improved method and system for treating lesions, especially calcified and/or fibrotic lesions.

SUMMARY

According to a first broad aspect, there is provided a method of treating a vascular lesion comprising: inserting a waveguide into a vessel of a subject, a lesion being present in the vessel and the waveguide extending longitudinally between a proximal end and a distal end; positioning the distal end of the waveguide adjacent to the lesion; generating a high amplitude mechanical pulse and propagating the high amplitude pulse from the proximal end to the distal end of the waveguide; and propagating at least a portion of the high amplitude pulse from the distal end of the waveguide to the lesion.

In some embodiments, the method further comprises imaging a portion of the body of the body comprising the vessel having the lesion therein.

In some embodiments, the step of inserting a waveguide comprises inserting a waveguide having a marker positioned at the distal end thereof.

In some embodiments, the method further comprising deflecting the at least a portion of the high amplitude mechanical pulse before reaching the lesion.

In some embodiments, the step of deflecting occurs at the distal end of the waveguide.

In some embodiments, the step of deflecting occurs away from the distal end of the waveguide.

In some embodiments, the step of generating comprises generating a plurality of mechanical waves having a first amplitude and combining the mechanical waves, thereby obtaining at least one high amplitude mechanical pulse each having a second amplitude greater than the first amplitude.

In some embodiments, the step of said combining comprises focusing the mechanical waves on a focus zone.

In some embodiments, the step of combining comprising propagating the mechanical waves into a temporal concentrator.

In some embodiments, the step of combining comprises propagating the mechanical waves in a taper.

In some embodiments, the step of combining comprises propagating the mechanical waves in a reverberating cavity In some embodiments, the step of combining comprises propagating the mechanical waves in a dispersive medium.

In some embodiments, the at least one high amplitude mechanical pulse each have a center frequency fc comprised between about 20 kHz and about 10 MHz and a duration of about 1/fc.

In some embodiments, an amplitude of the at least one high amplitude mechanical pulse when reaching the distal end of the transmission member is comprised between about 1 MPa and about 1000 MPa.

According to another broad aspect, there is provided a system for treating a vascular lesion, comprising: a pulse generator for generating at least one high amplitude and short duration mechanical pulse; and a waveguide extending between a proximal end and a distal end, the proximal end being coupled to the pulse generator for receiving the at least one mechanical pulse therefrom, the transmission member for propagating the at least one mechanical pulse from the proximal end to the distal end and transmitting the at least one mechanical pulse at the distal end, the distal end being adapted to be introduced into a vessel of a subject comprising the lesion In some embodiments, the pulse generator comprises: a plurality of broadband sources each for emitting a respective mechanical wave having a first amplitude; and a wave concentrator for combining the mechanical waves in order to obtain the mechanical pulse having a second amplitude greater than the first amplitude.

In some embodiments, the wave concentrator is a spatial concentrator.

In some embodiments, the wave concentrator is a temporal concentrator.

In some embodiments, the wave concentrator is adapted to focus the mechanical waves on a focus zone adjacent to the proximal end of the transmission member.

In some embodiments, the wave concentrator comprises a parabolic reflecting surface for reflecting at least some of the mechanical waves generated by the broadband sources towards the focus zone.

In some embodiments, the wave concentrator is a taper.

In some embodiments, the wave concentrator comprises a spatial concentration stage and a temporal concentration stage.

In some embodiments, the at least one high amplitude mechanical pulse each have a center frequency fc comprised between about 20 kHz and about 10 MHz and a duration of about 1/fc.

In some embodiments, an amplitude of the at least one high amplitude mechanical pulse when reaching the distal end of the transmission member is comprised between about 1 MPa and about 1000 MPa.

In some embodiments, the waveguide is flexible.

In some embodiments, the system further comprises a deflector for deflecting and orienting the mechanical pulse.

In some embodiments, the deflector is integral with the waveguide.

In some embodiments, the deflector comprises a beveled face.

In some embodiments, the deflector projects from the distal end of the waveguide.

In some embodiments, the deflector has a truncated conical shape.

In some embodiments, the deflector is independent from the waveguide.

A mechanical wave may have an arbitrary amplitude, duration, waveform, frequency, and/or the like. For example, a mechanical wave may have a high/low amplitude, a short/long duration, different waveforms, and any frequency content.

For the purpose of the present description, a mechanical pulse should be understood as a short duration mechanical wave. The duration of a mechanical pulse is of the order of about 1/fc.

Furthermore, a mechanical waveguide should be understood as a waveguide adapted to propagate mechanical waves or pulses along its length. In the present description, the expressions "waveguide", "mechanical waveguide" and "transmission member" may be used interchangeably. The shape and dimension of a waveguide may vary. For example, a waveguide may have a cylindrical shape. The diameter of the waveguide may be constant along its length. Alternatively, the diameter of the waveguide may vary along its length. For example, the diameter of a waveguide may decrease along its length so that the waveguide corresponds to a taper.

In one embodiment, a mechanical waveguide may comprise a single elongated element adapted to propagate mechanical waves and/or pulses therealong. In another embodiment, a mechanical waveguide may comprise a plurality of elongated elements each adapted to propagate mechanical waves and/or pulses therealong.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION

Figure 1:
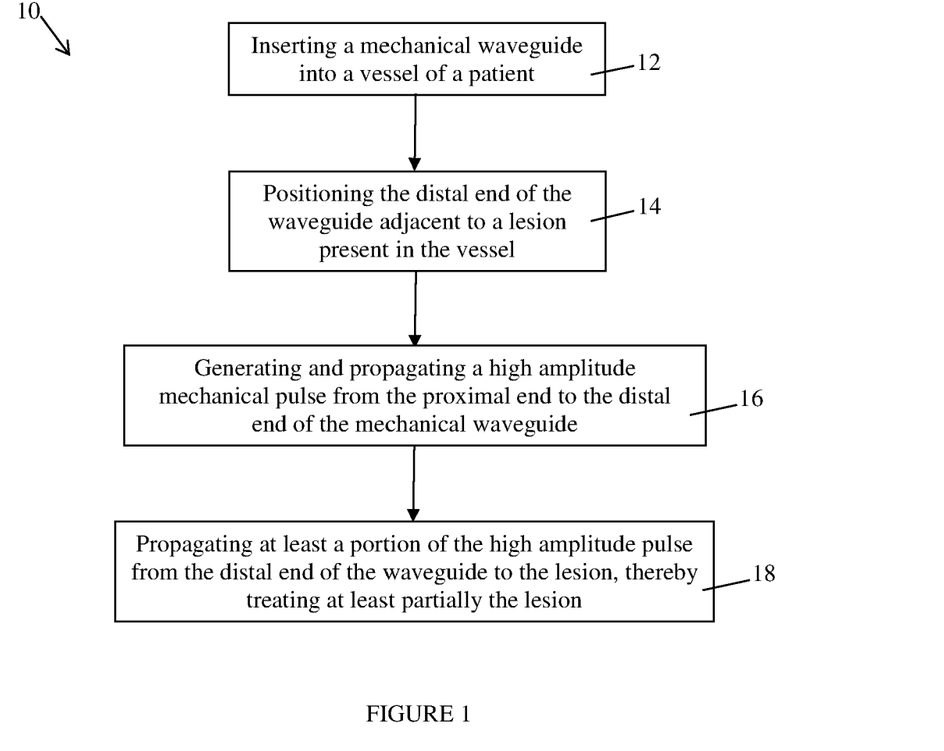
FIG. 1 is a flow chart of a method for treating a lesion present in a blood vessel, in accordance with an embodiment.

FIG. 1 illustrates one embodiment of a method 10 for treating a lesion such as a vascular lesion present in a vessel of a subject. Treating a lesion should be understood as at least one of at least partially cracking, eroding, cleaving, tunneling, crossing and breaking the lesion. The method 10 may have applications in fields other than the medical field. For example, the method may be used to cross lesions/obstructions present in a pipe that is used to propagate water or any other fluid.

At step 12, a mechanical waveguide or transmission member adapted to propagate mechanical waves and pulses is provided. The mechanical waveguide extends between a proximal end and a distal end. At step 12, the distal end of the mechanical waveguide is inserted into a blood vessel of the subject such as a vein, an artery or any other conduct present in a human body, the vessel comprising a lesion to be treated.

The mechanical waveguide is inserted into the vessel until the distal end of the mechanical waveguide is positioned adjacent to the lesion at step 14. In some embodiments, the distal end of the mechanical waveguide is positioned so as to abut against the lesion. In some other embodiments, the distal end of the mechanical waveguide is positioned so as not to be in physical contact with the lesion. In some other embodiments, the distal end of the mechanical waveguide is in lateral contact with the lesion.

Once the distal end of the mechanical waveguide has been positioned at an adequate position relative to the lesion, a mechanical pulse having a high amplitude and short duration is generated at step 16. The mechanical waveguide receives the generated mechanical pulse at the proximal end and the mechanical pulse propagates along the length of the mechanical waveguide up to the distal end. When it reaches the distal end, the mechanical pulse is transmitted at the distal end at step 18, which creates a displacement of the distal end and a mechanical pulse that propagates in the medium surrounding the distal end of the mechanical waveguide away from the distal end towards the lesion. In one embodiment, substantially all of the mechanical pulse is transmitted at the distal end of the mechanical waveguide. In another embodiment, only a portion of the mechanical pulse is transmitted at the distal end of the mechanical waveguide depending, among other things, on the acoustical impedance continuity at the interface between the distal end and the surrounding medium. While reaching the lesion, the mechanical pulse cracks, erodes, cleaves, tunnel, crosses and/or breaks at least partially the lesion.

In one embodiment, a train of successive mechanical pulses are generated at a given repetition rate during a given period of time. In this case, the steps 14 to 18 are repeated. In one embodiment, the repetition rate may be substantially constant in time. In another embodiment, the repetition rate may vary in time.

In one embodiment, the method further comprises a step of imaging a portion of the body of the subject that comprises the lesion to be treated. Any adequate method for imaging the lesion such as X-ray imaging, ultrasound imaging or magnetic imaging may be used. In one embodiment and as described below, the distal end of the mechanical waveguide is provided with a marker opaque to the radiation emitted during the imaging so that the marker appears on the taken images. In this case, the method 10 comprises a step of displaying on a display unit the images taken using the imaging technique to allow a user visualizing the position of the distal end of the mechanical waveguide relative to the lesion and therefore adequately positioning the distal end of the mechanical waveguide relative to the lesion.

In one embodiment, the outputs of several sources covering adjacent frequency bands are combined to generate the mechanical pulse. In one embodiment, the outputs of at least two broadband sources, i.e., the mechanical pulses generated by the at least two broadband sources, are combined. In another embodiment, the outputs of at least one broadband source and at least one narrowband source are combined.

In another embodiment, the mechanical pulse is generated by focusing, via a spatial concentrator, the output of a large broadband source toward a focal zone. It should be understood that the outputs of more than one large broadband source may be concurrently focused on the same focal zone.

In a further embodiment, a high amplitude mechanical pulse may be generated by spatially and/or temporally combining mechanical pulses or waves sequentially emitted by a single broadband source using a reverberating cavity. It should be understood that the mechanical pulses generated by more than one broadband source may be spatially and/or temporally combined together by a reverberating cavity to provide the high amplitude mechanical pulse.

In still another embodiment, high amplitude mechanical pulses may be generated by using a dispersive medium and/or a dispersive geometry to combine the component waves emitted sequentially by a single broadband source. It should be understood that the mechanical pulses generated by more than one source may be combined together using the dispersive medium or the dispersive geometry.

In one embodiment, the mechanical pulse has a center frequency fc comprised between about 20 kHz and about 10 MHz. In one embodiment, the amplitude of the high amplitude mechanical pulse is at least equal to 1 MPa. In one embodiment, the amplitude of the mechanical pulse when reaching the distal end of the transmission member is comprised between about 1 MPa and about 1000 MPa. In one embodiment, the duration of the short duration mechanical pulse when reaching the distal end of the transmission member is in the order of 1/fc.

In one embodiment, the method may be adapted to treat vascular lesions. In this case, when the distal end of the mechanical waveguide is positioned to be in physical contact with the lesion and a mechanical pulse reaches the distal end of the mechanical waveguide, the distal end will impact onto the lesion and transmits the mechanical pulse in the lesion itself. If the distal end of the transmission member is not in physical contact with the lesion, the mechanical pulse is transmitted in the medium present between the lesion and the distal end, e.g. blood, and the transmitted mechanical pulse can propagate up to the lesion. The mechanical pulse allows cracking, eroding cleaving, tunneling and/or breaking at least partially the lesion. For example, this may allow the distal end of the mechanical waveguide to cross, or traverse, the lesion as the distal end is moved farther within the vessel. A pressure force may be exerted on the mechanical waveguide while mechanical pulses are generated and transmitted to the lesion to help the distal end of the mechanical waveguide crossing the lesion.

In one embodiment, the method further comprises a step of amplifying the amplitude of the mechanical pulse. In an embodiment in which a temporal concentrator is present, the mechanical wave becomes a mechanical pulse of which the amplitude is greater than that of each component wave of the mechanical wave. In an embodiment in which a spatial concentrator is present, the amplitude of a mechanical pulse or wave is increased while propagating through the spatial concentrator. In another embodiment in which a spatial concentrator is present, different mechanical waves or pulses are combined to generate a greater amplitude mechanical wave or pulse, i.e. the different mechanical waves or pulses add to each other.

In one embodiment, the method further comprises imaging the portion of the subject body that comprises the lesion during the insertion of the mechanical waveguide using any adequate medical imaging method in order to allow a medical practitioner seeing the relative position between the distal end of the mechanical waveguide and the lesion. In some embodiments, X-ray imaging is used for imaging the lesion. In this case, the mechanical waveguide may be provided with a radiopaque marker positioned at the distal end thereof. The opaque marker is made of a material that blocks the propagation of X-rays so that the opaque marker be visible on an X-ray image.

In one embodiment, the method 10 further comprises a step of deflecting the mechanical pulse to orient the mechanical pulse in a predefined direction such as radially. In this case, the distal end of the mechanical waveguide is shaped and sized to orient the mechanical pulse in a given direction. For example, the distal end may be beveled to orient the mechanical in a given direction. In another example, the distal end of the mechanical waveguide may have a frusto-conical shape to radially emit the mechanical pulse. In another embodiment, a deflector adapted to reflect at least partially a mechanical wave or pulse may be used to deflect the mechanical pulse in a given direction. The deflector may be independent from the mechanical waveguide and positioned away from the distal end of the mechanical waveguide at an adequate position and according to an adequate orientation in order to direct the mechanical pulse towards the lesion.

In one embodiment, the mechanical waveguide is adapted to be inserted into a blood vessel, a catheter, a balloon catheter or the like. In this case, the mechanical waveguide is sized and shaped to slide into the blood vessel or the catheter. In one embodiment, the mechanical waveguide is made of a flexible material so that it may be bent to follow curvatures of the blood vessel or the like. In another embodiment, the mechanical waveguide may be built into a catheter or a balloon.

Figure 2:
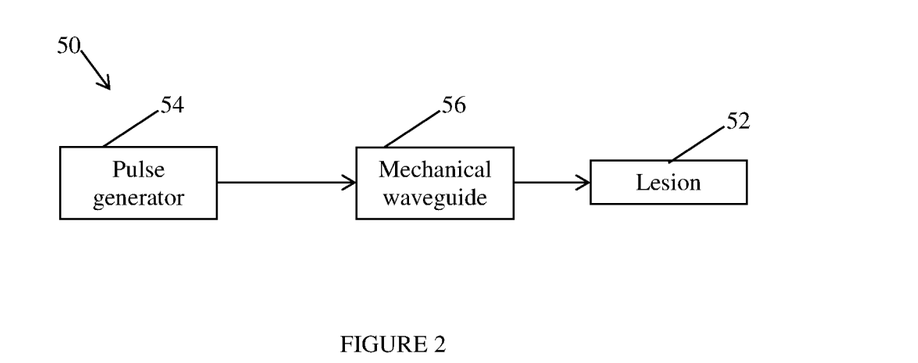
FIG. 2 is a block diagram illustrating a system for treating a lesion present in a vessel, the system comprising a source of mechanical pulses and a mechanical waveguide, in accordance with an embodiment.

FIG. 2 illustrates a system 50 for treating a lesion. The system 50 comprises a pulse generator 54 and a mechanical waveguide 56 adapted to propagate mechanical waves or pulses.

The pulse generator 54 is adapted to generate a high amplitude and short duration pulse. As described above, the pulse generator 54 may comprise at least one broadband source and/or at least one narrow band source. The narrow brand or broadband source may be an electromechanical transducer. The pulse generator 54 may comprise a spatial concentrator to focus the output of at least one source toward a focal zone at which the proximal end of the mechanical waveguide 56 is located so as to couple the generated pulse therein.

In some embodiments, the pulse generator 54 may comprise a spatial concentrator and/or a temporal concentrator for combining mechanical pulses or waves sequentially emitted by a single broadband source using a reverberating cavity.

In some embodiments, the pulse generator 54 may comprise a dispersive medium to combine the component waves emitted sequentially by a single broadband source.

The mechanical waveguide 56 extends between a first or proximal end that is operatively connected to the pulse generator 54 and a second or distal end 88. The transmission member 66 is adapted to receive mechanical pulses at its proximal end and propagate the mechanical pulses up to its distal end. When it reaches the distal end, the mechanical pulse is at least partially transmitted to generate a transmitted pulse that propagates outside of the mechanical waveguide 56. It should be understood that a pulse may also be reflected by the distal end and propagates back in the mechanical waveguide 56 towards the proximal end. The transmitted mechanical pulse corresponds to a mechanical pulse that propagates in the medium surrounding the distal end of the mechanical waveguide 56 up to the lesion 52. The transmitted pulse further propagates into the lesion 52, which may create cracks within the lesion 52, and eventually cleaves or breaks the lesion 52 into pieces. Also, as the pulse propagates along the mechanical waveguide 56, radial and longitudinal motion is induced at the surface of the mechanical waveguide 56 which reduces the friction between the mechanical waveguide 56 and the surrounding medium and facilitates the longitudinal displacement of the mechanical waveguide 56 into the medium, such as when crossing fibrotic tissue within a lesion.

In an embodiment in which the distal end of the mechanical waveguide 56 abuts against the lesion 52, the mechanical waveguide 56 may further be used to break the lesion 52 and/or drill a hole into the lesion 52. The transmission of the mechanical pulse at the distal end of the mechanical waveguide 56 creates a movement of the distal end of the mechanical waveguide 56. This movement may be along the longitudinal axis of the mechanical waveguide. Alternatively, the movement may be perpendicular to the longitudinal axis or it may be a combination of movements both along the longitudinal axis and perpendicular to the longitudinal axis of the mechanical waveguide. During this movement, the distal end of the mechanical waveguide 56 nominally first moves towards the lesion 52 and then moves back into its initial position. It should be understood that the movement may be inverted (i.e., the distal end may first move away from the lesion 52 and then towards the lesion 52) depending on the polarity of the mechanical pulse reaching the distal end of the mechanical waveguide 56. When a plurality of distinct mechanical pulses are successively transmitted at the distal end of the mechanical waveguide 56, the movement of the distal end may be seen as a jack-hammer movement which may be used to treat the lesion 52.

As the distal end of the mechanical waveguide 56 recesses (i.e., goes away from the lesion), a tension wave is created in the medium surrounding the distal end which may create a cavitation effect. If the medium is a fluid and since a fluid cannot withstand tensile forces, the fluid changes phase and vaporizes into microscopic bubbles (void and/or vapor). These bubbles are unstable and may collapse violently inducing powerful shock waves and velocity jets. The erosion capability of the induced shock waves and velocity jets may contribute to the ablation of the lesion 52.

In some embodiments, a first section of the mechanical waveguide 56 is inserted within the vessel which contains the lesion 52 and a second section of the mechanical waveguide 56 is located outside the vessel. In some embodiments, at least the first section of the mechanical waveguide 56 is adapted to be inserted into a blood vessel. For example, the first section of the mechanical waveguide 56 may comprise a biocompatible coating or be made of a biocompatible material. In some embodiments, only the first section of the mechanical waveguide 56 may be flexible. In one embodiment, the mechanical waveguide may be built or insertable into a catheter or balloon.

The following describes the operation of the system 50. A first section of the mechanical waveguide 56 is inserted into a vessel containing a lesion 52 so that the distal end of the mechanical waveguide 56 is adjacent to the lesion 52. In one embodiment, the mechanical waveguide 56 is positioned so that its distal end substantially abuts against the lesion 52 or be in lateral contact with the lesion 52 or at an adequate position relative to the lesion 52.

As described above, the transmitted pulse propagates up to the lesion 52 and if the distal end of the mechanical waveguide 56 abuts against the lesion 52 or is in lateral contact with the lesion 52, the jackhammer movement created by the multiple mechanical pulses at the distal end may be used to treat the lesion 52.

The distal end of the mechanical waveguide 56 is used to emit the mechanical pulses from the mechanical waveguide 56 core toward the lesion 52. The distal end may also be used to create a path and navigate through the lesion 52, enlarge the diameter of the path, and/or orient the direction of the emitted mechanical pulses.

In an embodiment in which the mechanical waveguide 56 is to be inserted into a catheter, the distal end of the mechanical waveguide 56 may be designed as to facilitate its introduction into the catheter toward the lesion. In one embodiment, a hydrophobic coating may be applied at the distal end of the transmission member to improve its lubricity and in some instance to flush the blood out of the catheter as the distal end advances toward the lesion 52 and thereby reduce the quantity of blood that surrounds the mechanical waveguide 56 which could contribute to energy leakage. In one embodiment, a hydrophilic coating is added at the distal end of the mechanical waveguide 56 to facilitate its introduction in a catheter and/or its penetration into the lesion. The mechanical waveguide may be positioned near the lesion by itself or into or around another device such as a guidewire, catheter or balloon, already present near the lesion.

In one embodiment, an acoustic coupler is secured to the distal end of the mechanical waveguide 56 in order to decrease the acoustic impedance mismatch between the distal end of the mechanical waveguide and its surroundings which increases the energy transmission from the mechanical waveguide 56 towards the lesion 52.

In one embodiment, radiopaque markers such as tungsten, gold strips, high-density plating, high-density ring, high-density coil or doped polymer jacket with dense metal powders are secured to the distal end of the mechanical waveguide 56 to serve as references points in order to visualize via X-rays the position of the distal end relative to the lesion 52 and to other PTA devices. It should be understood that the marker may be made of a material that is opaque to an imaging technique other than X-ray such as ultrasound, magnetic resonance, or the like. When ultrasound imaging is used, the marker may comprise void or gas bubbles secured at the distal end of the mechanical waveguide 56 so as to be opaque to ultrasound and help a user visualizing the distal end of the mechanical waveguide 56 relative to the lesion to be treated.

In one embodiment, the system 50 further comprises a deflector for deflecting or orienting the mechanical pulse and/or the mechanical waveguide distal end. In some embodiments, the deflector may be independent from the mechanical waveguide 56. In other embodiments, the deflector may be integral with the mechanical waveguide 56. In still another embodiment, the distal end of the transmission member may be curved to allow deflecting and/or orienting the mechanical pulse.

Figure 3:
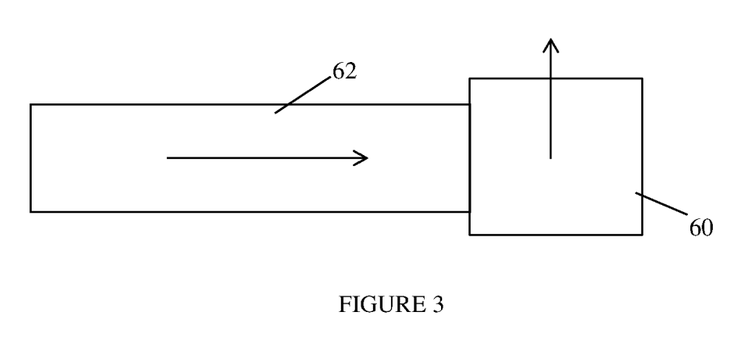
FIG. 3 is a block diagram illustrating a mechanical waveguide and a deflector for deflecting a mechanical pulse coming from the mechanical waveguide, in accordance with an embodiment.

FIG. 3 illustrates one embodiment of a generic deflector 60 that is used to deflect a mechanical pulse outputted by a mechanical waveguide 62 according to a predefined direction. For example, the deflector 60 may be adapted to deflect the mechanical pulse radially around the longitudinal axis of the mechanical waveguide 62. In this embodiment, the deflector 60 is independent from the mechanical waveguide 62 while being in physical contact with the mechanical waveguide 62. For example, the deflector 60 may be secured at the distal end of the mechanical waveguide 62.

Figure 4:
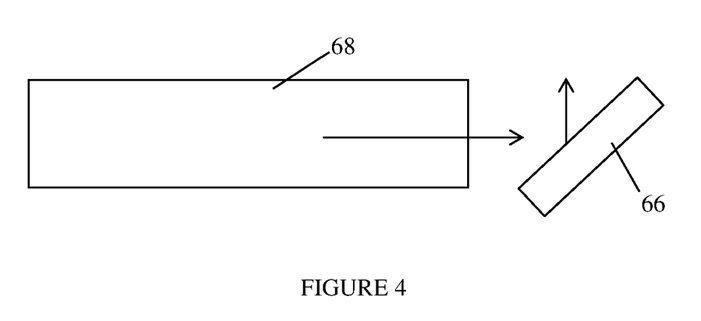
FIG. 4 is a block diagram illustrating a mechanical waveguide and a deflector angularly positioned relative to the mechanical waveguide so as to deflect a mechanical pulse coming from the mechanical waveguide, in accordance with an embodiment.

FIG. 4 illustrates one embodiment of a deflector 66 that may be used in connection with a mechanical waveguide 68 having a flat distal end. The flat surface of the distal end is substantially orthogonal to the outer longitudinal surface of the mechanical waveguide 66 that extends along the length thereof in order to maximize the energy output along the longitudinal axis along which the mechanical waveguide 68 extends. In the illustrated embodiment, the deflector 66 is positioned angularly relative to the longitudinal axis of the mechanical waveguide 68 and away from the distal end of the mechanical waveguide 68.

In some embodiments, the deflector 66 may be secured to the mechanical waveguide 68.

Figure 5:
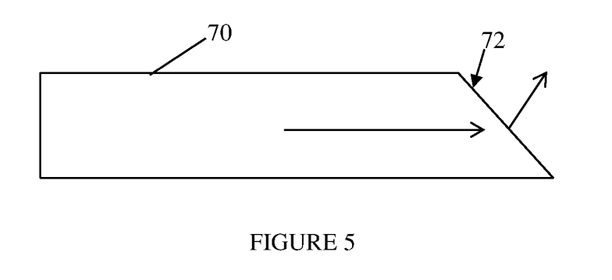
FIG. 5 illustrates a mechanical waveguide extending between a proximal end and a distal end, the distal end being beveled, in accordance with an embodiment.

In other embodiments, the deflector may be integral with the mechanical waveguide. FIG. 5 illustrates one embodiment of a mechanical waveguide 70 having a distal flat and beveled end 72. The flat surface of the distal end 72 is beveled or at an angle with respect to the longitudinal axis. The angle is chosen so as to orient the propagated mechanical pulse according to a given direction. Such shape may also propel the mechanical waveguide sideways resulting in a slapping effect that may be used to the lesion, for example before the use of a balloon during PTA intervention.

It should be understood that the distal end of the mechanical waveguide may be provided with any adequate shape other than a flat shape. For example, the distal end may be provided with a rounded shape such as a hemi-spherical shape. The surface of the distal end may be provided with any adequate shape between a rounded shape and a flat shape. For example, the surface of the distal end may be substantially planar with a smoothed or rounded edge to be as atraumatic as possible for biological tissues. In another example, the distal end maybe provided with a shape to focus the mechanical energy away from the distal end. This focusing shape could be a concave shape, for example a circular or parabolic shape. This focusing shape could be such as to focus the mechanical pulse along the longitudinal axis of the transmission member, or away from this same axis.

In one embodiment, the distal end of the mechanical waveguide 56 may be shaped so as to direct the mechanical pulse at least partially radially. This configuration may be used to create a path in the lesion 52 with a diameter larger than that of the distal end. Moreover, such embodiment may be used to prepare the lesion site prior the use of balloon during a PTA intervention.

In one embodiment, the distal end of the mechanical waveguide 56 may be shaped (such as flutes on a drill bit) so as to ease the evacuation of lesion debris as the mechanical waveguide progresses in the lesion.

Figure 7:
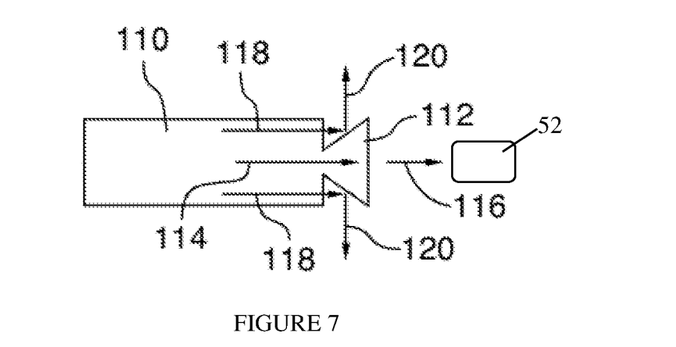
FIG. 7 illustrates a mechanical waveguide extending between a proximal end and a distal end, the distal end being provided with a frusto-conical structure to deflect mechanical pulses, in accordance with an embodiment.

FIG. 7 illustrates such a configuration in which a mechanical waveguide 110 is provided with a distal end adapted to partially emit a radial mechanical wave. A protrusion 112 having a truncated conical shape protrudes from the distal end of the mechanical waveguide 110. The protrusion 112 extends between a circular distal wall located away from the mechanical waveguide 110 and a circular proximal wall secured to the waveguide 110. A truncated conical wall extends between the circular proximal and distal walls. In the illustrated embodiment, the mechanical waveguide 110 and the protrusion 112 are coaxial.

Figure 6A:
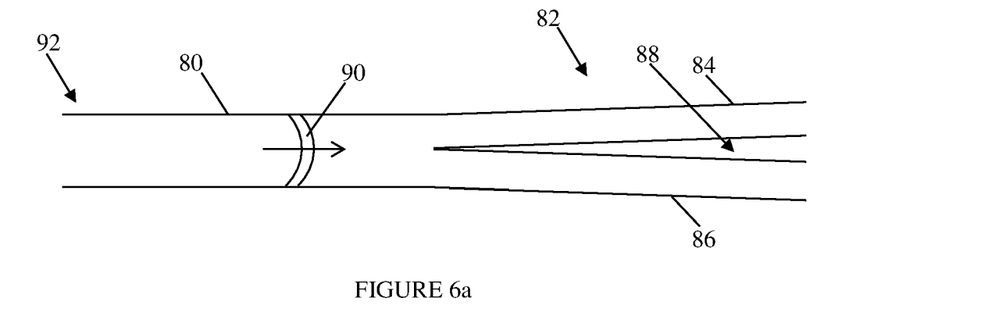
FIG. 6a illustrates a mechanical waveguide provided with a divided distal end in a first configuration, in accordance with an embodiment.
Figure 6B:
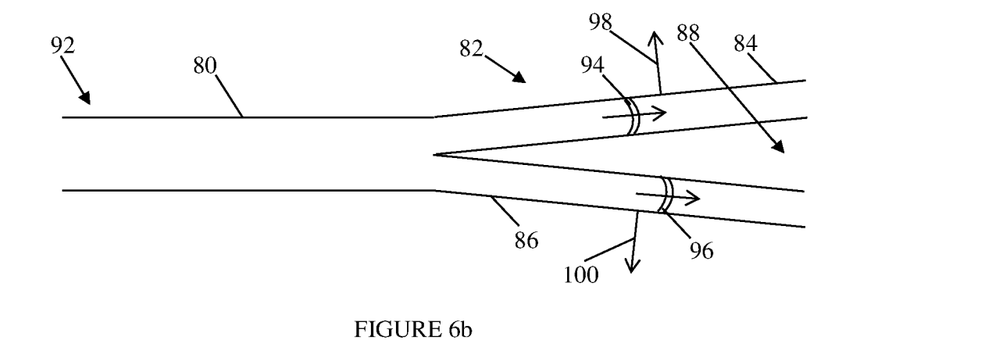
FIG. 6b illustrates the mechanical waveguide of FIG. 6a in a second configuration.

In another configuration, the distal tip of the mechanical waveguide could be split into regions along a direction essentially parallel to its longitudinal axis, such that when the mechanical pulse reaches this region it forces the various regions away from the split interface, enabling some redirection of some of the energy in the radial direction. FIGS. 6a and 6b illustrate one exemplary embodiment for such a mechanical waveguide 80. The distal end 82 of the mechanical waveguide 80 is divided into two regions or two secondary mechanical waveguides 84 and 86. A gap 88 is located between the two secondary mechanical waveguides 84 and 86. In FIG. 6a, a mechanical pulse 90 propagates into the mechanical waveguide 80 from its proximal end 92 towards its distal end 82. When reaching the junction between the two secondary mechanical waveguides 84 and 86, the mechanical pulse 90 is divided into a first mechanical pulse 94 which propagates into the secondary mechanical pulse 84 and a second mechanical pulse 96 which propagates into the secondary mechanical waveguide 86. The propagation of the mechanical pulses 94 and 96 in the secondary mechanical pulses 84 and 86 forces the secondary mechanical waveguides 84 and 86 to move away from one another as illustrated by arrows 98 and 100, as illustrated in FIG. 6b. As a result, the gap 88 between the two secondary mechanical waveguides 84 and 86 increases, thereby allowing directing some the mechanical energy in the radial direction.

In another configuration, the distal tip of the mechanical waveguide could be alternately curved along the longitudinal axis so as to redirect some of the mechanical energy in the radial direction. However, the person skilled in the art will understand that other configurations may be possible.

As illustrated in FIG. 6, the central portion of the mechanical energy schematically represented by arrow 114 propagates through the protrusion 112 to generate a longitudinal mechanical wave schematically represented by arrow 116 that propagates substantially along the longitudinal axis of the waveguide 110 outside of the waveguide 110 towards the lesion 52. The outer portion of the mechanical energy schematically represented by arrow 118 and adjacent to the outer surface of the waveguide 110 propagates outside of the waveguide 110 and is reflected by the truncated conical wall of the protrusion 112 to generate a radial mechanical wave.

While in the illustrated embodiment, the propagation direction of the radial mechanical wave is substantially orthogonal to that of the longitudinal mechanical wave, it should be understood that other configurations are possible by varying the angle between the waveguide 110 and the truncated conical wall of the protrusion 112. Moreover, such configuration does not need to be symmetrical around the main axis of the mechanical waveguide.

The person skilled in the art will understand that the amount of energy converted into a radial mechanical wave may be adjusted by adequately varying the surface area of the distal and/or proximal walls of the protrusion 112.

In one embodiment the section of the mechanical waveguide adjacent to the distal end may be bent or bendable so that a user may apply a permanent or temporary curvature with his fingers, a metallic needle introducer or a tool. A bent at the distal end may be used to steer the mechanical waveguide (i.e., to give the mechanical waveguide a direction) as it is pushed forward in the blood vessel or in the lesion and/or to redirect the emitted mechanical pulse.

In one embodiment, the mechanical waveguide has a cross-sectional shape and/or cross-sectional dimensions that are substantially constant along a length thereof. For example, the mechanical waveguide may have a circular cross-sectional shape of which the diameter is substantially constant along the length thereof. In one embodiment, the diameter of the waveguide is between about 0.004 and about 0.035 in.

In another embodiment, the cross-sectional shape and/or the dimensions of the mechanical waveguide may vary along a length thereof. For example, the first section of the mechanical waveguide that is adjacent to the proximal end and/or the second section of the mechanical waveguide that is adjacent to the distal end may have a cross-sectional shape and/or a dimension different from a third section located between the first and second sections. In another example, the mechanical waveguide may comprise at least one tapering section for amplifying mechanical pulses.

In one embodiment, the mechanical waveguide is adapted to be used with traditional PTA devices. In one embodiment, the mechanical waveguide has a diameter that is less than about 0.125 inches, and preferably less than about 0.040 inches. In one embodiment, the aspect ratio (defined as: length/diameter) of the mechanical waveguide is chosen to be greater than 100, and preferably greater than 1000. In one embodiment, the mechanical waveguide has a length comprised between about 60 in and about 120 in. In another embodiment, the mechanical waveguide has a length comprised between about 36 in and about 200 in.

In one embodiment, the bandwidth of the energy source used in the present system, which is expressed as a percentage of the center frequency fc, is greater than about 10%, and preferably between about 40% and about 120%. The center/main frequency fc of the broadband energy source may vary between about 20 kHz and about 10 MHz and is preferably between about 0.1 MHz and about 1 MHz.

The broadband source power and the level of control over the output of the broadband source can be characterized by the pulse duration, repetition rate, pressure amplitude, polarity and waveform type. In one embodiment, the mechanical pulse duration at the distal end of the transmission member is usually of the order of $1/f_c$. For example, an energy source having a center frequency of 500 kHz will generate a mechanical pulse having duration of about 2 µs, when a bandwidth of 100% is considered. In one embodiment, the mechanical pulse duration can be varied by changing the center frequency or the bandwidth (i.e., Q factor) of the energy source; the pulse duration is preferably less than about 1 ms.

The pulse repetition rate is associated with the number of pulses that can be transmitted during a certain amount of time. In one embodiment, the repetition rate can be varied between about 0.1 Hz and about 1000 Hz and is preferably between about 10 Hz and about 200 Hz.

In one embodiment, the output pressure amplitude of the mechanical pulse generated at the output of the transmission member is greater than about 10 MPa in both compression and tension. In one embodiment, the output pressure amplitude is comprised between about 10 MPa and about 1000 MPa in compression and between about 10 MPa and about 500 MPa in tension, when measured at the distal end of the transmission member in a fluid medium.

Pulsed and controlled mechanical wave emission at the distal end of the transmission member may crack, cleave, erode, tunnel and/or break parts of the lesion. By doing so, the lesion is easier to treat using the present system and method than traditional PTA devices.

In one embodiment, the distal end of the mechanical waveguide is adapted to cross at least one of a fibrotic tissue and a calcified tissue contained within a lesion. In another embodiment, the distal end of the mechanical waveguide is adapted to crack and/or break at least one of a fibrotic tissue and a calcified tissue contained within an lesion positioned laterally to the distal end of the mechanical waveguide.

The embodiments of the invention described above are intended to be exemplary only. The scope of the invention is therefore intended to be limited solely by the scope of the appended claims.

We claim:

1. A method of treating a lesion comprising:
   inserting a mechanical waveguide into a vessel of a body of a subject, a lesion being present in the vessel and the mechanical waveguide extending longitudinally between a proximal end and a distal end;
   positioning the distal end of the mechanical waveguide adjacent to the lesion;
   generating, using a pulse generator operatively connected to the proximal end of the mechanical waveguide, a high amplitude broadband mechanical pulse and propagating the high amplitude broadband mechanical pulse from the proximal end to the distal end of the mechanical waveguide; and
   propagating at least a portion of the high amplitude broadband mechanical pulse from the distal end of the mechanical waveguide to the lesion, the at least a portion of the high amplitude broadband mechanical pulse propagating up to the lesion, thereby treating at least partially the lesion.

2. The method of claim 1, further comprising imaging a portion of the body comprising the vessel having the lesion therein.

3. The method of claim 2, wherein said inserting the mechanical waveguide comprises inserting the mechanical waveguide having a marker positioned at the distal end thereof.

4. The method of claim 1, further comprising deflecting the at least a portion of the high amplitude broadband mechanical pulse before reaching the lesion.

5. The method of claim 4, wherein said deflecting occurs at the distal end of the mechanical waveguide.

6. The method of claim 4, wherein said deflecting occurs away from the distal end of the mechanical waveguide.

7. The method of claim 1, wherein said generating comprises generating a plurality of broadband mechanical waves having a first amplitude and combining the plurality of broadband mechanical waves, thereby obtaining the high amplitude broadband mechanical pulse having a second amplitude greater than the first amplitude.

8. The method of claim 7, wherein said combining the plurality of broadband mechanical waves comprises focusing the plurality of broadband mechanical waves on a focus zone.

9. The method of claim 7, wherein said combining the plurality of broadband mechanical waves comprises propagating the plurality of broadband mechanical waves into a temporal concentrator.

10. The method of claim 7, wherein said combining the plurality of broadband mechanical waves comprises propagating the plurality of broadband mechanical waves in a taper.

11. The method of claim 7, wherein said combining the plurality of broadband mechanical waves comprises propagating the plurality of broadband mechanical waves in a reverberating cavity.

12. The method of claim 7, wherein said combining the plurality of broadband mechanical waves comprises propagating the plurality of broadband mechanical waves in a dispersive medium.

13. The method of claim 1, wherein the high amplitude broadband mechanical pulse has a center frequency fc comprised between about 20 kHz and about 10 MHz and a duration of about 1/fc.

14. The method of claim 1, wherein an amplitude of the high amplitude broadband mechanical pulse when reaching the distal end of the mechanical waveguide is comprised between about 1 MPa and about 1000 MPa.

15. The method of claim 1, wherein said positioning the distal end of the mechanical waveguide adjacent to the lesion comprises positioning the distal end of the mechanical waveguide to be in contact with the lesion in the blood vessel.

16. A system for treating a lesion, comprising:
   a pulse generator for generating at least one high amplitude broadband mechanical pulse; and
   a mechanical waveguide extending between a proximal end and a distal end, the proximal end being coupled to the pulse generator for receiving the at least one high amplitude broadband mechanical pulse therefrom, the mechanical waveguide for propagating the at least one high amplitude broadband mechanical pulse from the proximal end to the distal end and transmitting the at least one high amplitude broadband mechanical pulse at the distal end, the distal end being adapted to be introduced into a vessel of a subject comprising the lesion.

17. The system of claim 16, wherein the pulse generator comprises:
   a plurality of broadband sources each for emitting a respective mechanical wave having a first amplitude; and
   a wave concentrator for combining the respective mechanical waves in order to obtain the at least one high amplitude broadband mechanical pulse having a second amplitude greater than the first amplitude.

18. The system of claim 17, wherein the wave concentrator is a spatial concentrator.

19. The system of claim 17, wherein the wave concentrator is a temporal concentrator.

20. The system of claim 17, wherein the wave concentrator is adapted to focus the respective mechanical waves on a focus zone adjacent to the proximal end of the mechanical waveguide.

21. The system of claim 20, wherein the wave concentrator comprises a parabolic reflecting surface for reflecting at least some of the respective mechanical waves generated by the plurality of broadband sources towards the focus zone.

22. The system of claim 17, wherein the wave concentrator is a taper.

23. The system of claim 17, wherein the wave concentrator comprises a spatial concentration stage and a temporal concentration stage.

24. The system of claim 16, wherein the at least one high amplitude broadband mechanical pulse each have a center frequency fc comprised between about 20 kHz and about 10 MHz and a duration of about 1/fc.

25. The system of claim 16, wherein an amplitude of the at least one high amplitude broadband mechanical pulse when reaching the distal end of the mechanical waveguide is comprised between about 1 MPa and about 1000 MPa.

26. The system of claim 16, wherein the mechanical waveguide is flexible.

27. The system of claim 16, further comprising a deflector for deflecting and orienting the at least one high amplitude broadband mechanical pulse.

28. The system of claim 27, wherein the deflector is integral with the mechanical waveguide.

29. The system of claim 28, wherein the deflector comprises a beveled face.

30. The system of claim 27, wherein the deflector projects from the distal end of the mechanical waveguide.

31. The system of claim 30, wherein the deflector has a truncated conical shape.

32. The system of claim 27, wherein the deflector is independent from the mechanical waveguide.

33. The system of claim 16, wherein the distal end of the waveguide is positionable to be in contact with the lesion in the blood vessel.

* * * * *